United States Patent
Yamamoto et al.

(10) Patent No.: US 7,223,468 B2
(45) Date of Patent: May 29, 2007

(54) MEDICAL PRESSURE-SENSITIVE ADHESIVE SHEETS AND METHOD FOR PRODUCING THE SAME

(75) Inventors: Yuko Yamamoto, Osaka (JP); Kenji Furumori, Osaka (JP); Katsuhiro Okada, Osaka (JP)

(73) Assignee: Nitto Denko Corporation, Osaka (JP)

( * ) Notice: Subject to any disclaimer, the term of this patent is extended or adjusted under 35 U.S.C. 154(b) by 97 days.

(21) Appl. No.: 10/977,912

(22) Filed: Oct. 28, 2004

(65) Prior Publication Data

US 2005/0112367 A1  May 26, 2005

(30) Foreign Application Priority Data

Nov. 6, 2003  (JP) .............................. 2003-376930

(51) Int. Cl.
*B32B 7/12* (2006.01)
*A61L 15/58* (2006.01)
*C09J 7/04* (2006.01)

(52) U.S. Cl. ................ 428/355 AC; 428/343; 428/354; 604/289; 604/304; 604/307

(58) Field of Classification Search ................ 604/307, 604/304, 289; 428/343, 354, 355 AC
See application file for complete search history.

(56) References Cited

U.S. PATENT DOCUMENTS 4,564,010 A * 1/1986 Coughlan et al. ........... 604/307
4,909,243 A * 3/1990 Frank et al. ................... 602/58
5,092,323 A * 3/1992 Riedel et al. .................. 602/54
2005/0112367 A1 * 5/2005 Yamamoto et al. .......... 428/343

FOREIGN PATENT DOCUMENTS

JP    6-23029 A    2/1994
JP    6-319793 A   11/1994

OTHER PUBLICATIONS

Machine Translations of the Claims and Detailed Description of JP Abstract Publications 06-319793 and 06-023029.*

* cited by examiner

*Primary Examiner*—Daniel Zirker
(74) *Attorney, Agent, or Firm*—Frishauf, Holtz, Goodman & Chick, P.C.

(57) ABSTRACT

Medical pressure-sensitive adhesive sheets having a pressure-sensitive adhesive layer on at least one side of a support so as to have an appropriate tack strength and acceptable processability. The pressure-sensitive adhesive layer is formed with a pressure-sensitive adhesive composed mainly of an acrylic polymer and a compatible component that is compatible with the acrylic polymer. The support layer contains a compatible component that is compatible with the acrylic polymer. The amount of the compatible component contained in the support layer is 70% or less of the amount of the compatible component contained in the pressure-sensitive adhesive layer and the support layer has an elongation of 200% or more without containing any compatible component.

10 Claims, No Drawings

MEDICAL PRESSURE-SENSITIVE ADHESIVE SHEETS AND METHOD FOR PRODUCING THE SAME

BACKGROUND OF THE INVENTION

1. Field of the Invention

The present invention relates to pressure-sensitive adhesive sheets for use in the field of medical hygiene materials and more particularly to medial pressure-sensitive adhesive sheets for use in first-aid adhesive bandages, large adhesive bandages, pressure-sensitive bandages, dressing materials and the like.

2. Description of Related Art

Pressure-sensitive adhesives commonly used for the pressure-sensitive adhesive layers of pressure-sensitive adhesive tapes include pressure-sensitive adhesives comprised by (meth)acrylate polymers that have excellent adhesion and excellent moisture permeability as well as low chemical stimulation to the skin. Incidentally, the pressure-sensitive adhesives comprised by (meth)acrylate polymers may often cause users to feel pain or give damage to the corneum or epidermis of the skin when the pressure-sensitive adhesive tape if peeled from the skin because of strong adhesion of the adhesives comprised by the (meth)acrylate polymers. In particular, when pressure-sensitive adhesive tapes are applied to the same site repeatedly, damage of the skin accompanied by bleeding could occur, which raises a big problem.

To reduce such physical stimulations to the skin, there have been proposed pressure-sensitive adhesives obtained by adding, to a (meth)acrylate polymer, a large amount of liquid component compatible with the polymer, and subjecting the resultant to crosslinking treatment to bring it into a gel state as described in JP-A-06-23029 and JP-A-06-319793. For example, such pressure-sensitive adhesives can alleviate and scatter the stress given to the surface of the skin at the time of peeling off while retaining high adhesion attributable to the (meth)acrylate polymer. Therefore, the adhesives have less physical stimulation to the skin and do not cause peeling-off of the corneum and the like, so that they are used in transdermal drug delivery patches and medical surgical tapes.

However, lamination of the pressure-sensitive adhesive disclosed in the above-mentioned publications on films to form pressure-sensitive adhesive tapes results in migration of the liquid components in the pressure-sensitive adhesive into the films to swell the films, thus causing deformation. As a result, the processability of the pressure-sensitive adhesive sheets by, for example, punching is extremely reduced.

SUMMARY OF THE INVENTION

Under the circumstances, the present invention has been made and it is an object of the present invention to provide medical pressure-sensitive adhesive sheets that have appropriate tack strength and acceptable processability so that physical stimulation given to an adherend when they are peeled from the adherend can be maintained to low levels and of which supports do not undergo swelling deformation. It is also an object of the present invention to provide a method for producing such medical pressure-sensitive adhesive sheets.

To achieve the above-mentioned objects, the medical pressure-sensitive adhesive sheet of the present invention includes a support layer having a pressure-sensitive adhesive layer on at least one side thereof, wherein the pressure-sensitive adhesive layer is formed with an adhesive composed mainly of 100 parts by weight of an acrylic polymer and 30 to 100 parts by weight of a compatible component that is compatible with the acrylic copolymer and that is in liquid or paste state at room temperature and wherein the support layer contains a compatible component that is compatible with the acrylic polymer and that is in a liquid or paste state at room temperature, the amount of the compatible component contained in the support layer is 70% or less of the amount of the compatible component contained in the pressure-sensitive adhesive layer, and the support layer has an elongation of 200% or more in a state where the support layer contains no compatible component.

Here, it is preferable that the compatible component contained in the support layer and the compatible component contained in the pressure-sensitive adhesive layer have the same composition.

The compatible component may be an ester of a monobasic acid having 8 to 18 carbon atoms or a polybasic acid having 8 to 18 carbon atoms with a branched alcohol having 14 to 18 carbon atoms, and/or an ester of an unsaturated fatty acid having 14 to 18 carbon atoms or a branched acid having 14 to 18 carbon atoms with a tetrahydric or lower alcohol.

Further, 40 to 80% by weight of the acrylic polymer contained in the pressure-sensitive adhesive layer may be insolubilized.

Further, the support layer may be formed with a resin composition that contains a urethane-acrylic composite polymer.

The method for producing a medical pressure-sensitive adhesive sheet of the present invention includes coating at least a coating solution for a pressure-sensitive adhesive layer on a release treated surface of a release material, drying the coating solution to form a pressure-sensitive adhesive layer, while separately coating a coating solution for a support layer on a release treated surface of a release material, drying the coating solution to form a support layer, transferring the formed pressure-sensitive adhesive layer onto the support layer, thereby forming a medical pressure-sensitive adhesive sheet.

DETAILED DESCRIPTION

The medical pressure-sensitive adhesive sheet of the present invention has a pressure-sensitive adhesive layer on at least one side of the support layer. The support layer and pressure-sensitive adhesive layer each contain a compatible component that is compatible with the acrylic polymer and is in a liquid or paste state at room temperature. Here, it is preferable that the compatible components contained in the respective layers have the same composition. Note that the term "sheet" or "sheets" as used herein refers to sheet(s), film(s), tape(s) and so on.

The pressure-sensitive adhesive layer is formed with a pressure-sensitive adhesive that contains an acrylic polymer and a compatible component as major ingredients. The acrylic polymer is composed mainly of (meth)acrylates and optionally copolymerized with monomers that are copolymerizable with the (meth)acrylates.

The (meth)acrylates that can be used preferably include (meth)acrylates having 2 or more carbon atoms in the alkyl group and more preferably (meth)acrylates having 2 or more and 15 or less carbon atoms in the alkyl group. Specific examples of such alkyl group include linear or branched alkyl groups such as ethyl (meth)acrylate, propyl (meth)acrylate, n-butyl (meth)acrylate, isobutyl (meth)acrylate, pentyl (meth)acrylate, hexyl (meth)acrylate, heptyl (meth) acrylate, octyl (meth)acrylate, isooctyl (meth)acrylate, 2-ethylhexyl (meth)acrylate, nonyl (meth)acrylate, isononyl (meth)acrylate, decyl (meth)acrylate, undecyl (meth)acrylate, and tridecyl (meth)acrylate. In the present invention, alkyl (meth)acrylates having these alkyl groups may be used singly or as combinations of two or more of them.

The monomers that are copolymerizable with the (meth) acrylates include, for example, carboxyl group-containing monomers such as (meth)acrylic acid, itaconic acid, maleic acid, and maleic anhydride; sulfoxyl group-containing monomers such as styrenesulfonic acid, allylsulfonic acid, sulfopropyl (meth)acrylate, (meth)acryloyloxynaphthalenesulfonic acid, and acrylamidemethylpropanesulfonic acid; hydroxyl group-containing monomers such as hydroxyethyl (meth)acrylate and hydroxypropyl (meth)acrylate; amido group-containing monomers such as (meth)acrylamide, dimethyl (meth)acrylamide, N-butylacrylamide, N-methylol (meth)acrylamide and N-methylolpropane(meth)acrylamide; alkylaminoalkyl group-containing monomers such as aminoethyl (meth)acrylate, dimethylaminoethyl (meth)acrylate, and tert-butylaminoethyl (meth)acrylate; alkoxyalkyl (meth)acrylate such as methoxyethyl (meth)acrylate and ethoxyethyl (meth)acrylate; alkoxy group (or ether bond in the side chain)-containing (meth)acrylate such as methoxyethylene glycol (meth)acrylate, tetrahydrofurfuryl (meth) acrylate, methoxydiethylene glycol (meth)acrylate, methoxypolyethylene glycol (meth)acrylate, and methoxypolypropylene glycol (meth)acrylate; vinyl monomers such as (meth)acrylonitrile, vinyl acetate, vinyl propionate, N-vinyl-2-pyrrolidone, methylvinylpyrrolidone, vinylpyridine, vinylpiperidine, vinylpyrimidine, vinylpiperazine, vinylpyrazine, vinylpyrrole, vinylimidazole, vinylcaprolactam, vinyloxazole, and vinylmorpholine; and so on. In the present invention, one or more of these monomers may be used for copolymerization.

The monomers copolymerizable with the (meth)acrylates can be used in order to adjust cohesive force of the pressure-sensitive adhesive or to improve the compatibility of the compatible component in a liquid or paste state. The amounts of such copolymerizable monomers used may be appropriate set depending on the purpose and the like.

From the viewpoints of control of the amount of crosslinking sites of the pressure-sensitive adhesive and adjustment of the adhesive properties, the acrylic copolymers are preferably those formed from alkyl (meth)acrylate and at least one of the above-mentioned carboxyl group-containing monomer and hydroxyl group-containing monomer and optionally the above-mentioned copolymerizable monomer.

It is desirable that the acrylic polymer has a glass transition temperature of 260K or less. By adjusting the glass transition temperature of acrylic polymer to 260K or less, the adhesive can exhibit the property of adhesion to the skin sufficiently so that it can give rise to a desirable pressure-sensitive adhesive layer the resulting pressure-sensitive adhesive sheets for medical material or hygine material.

The acrylic polymer can be obtained by a known polymerization method such as a solution polymerization method, an emulsion polymerization method, a suspension polymerization method or the like. Further, it can also be obtained by performing a radical polymerization method using a radical polymerization initiator such as peroxide compound or an azo compound.

The pressure-sensitive adhesive layer contains a compatible component that is compatible with the acrylic polymer and is in a liquid or paste state at room temperature.

Blending the compatible component in the acrylic polymer reduces the modulus of the pressure-sensitive adhesive in a low deformation region, so that it can retain acceptable adhesion to the skin and gives less damage to corneum and reduced pain when it is peeled off. Therefore, the compatible component must be in a liquid or paste state in a temperature range in which it is practically used and must have good compatibility with the acrylic polymer. It is preferable that the compatible component is difficult to be transferred to medical instruments, medical devices and the like.

The compatible components that can be used include esters of monobasic or polybasic acids having 8 to 18 carbon atoms and branched alcohols having 14 to 18 carbon atoms, and/or esters of unsaturated fatty acids or branched acids having 14 to 18 carbon atoms and tetrahydric or lower alcohols.

Use of monobasic or polybasic acids having less than 8 carbon atoms may cause migration of much pressure-sensitive adhesive to medical instruments, medical devices and the like. On the other hand, use of monobasic or polybasic acids having more than 18 carbon atoms may result in reduction in the compatibility with the acrylic polymer, thus failing to give acceptable pressure-sensitive properties. Accordingly, it is preferable that monobasic or polybasic acids having 8 to 18 carbon atoms are used. Further, use of branched alcohol having less than 14 carbon atoms that is in a liquid state at room temperature may allow migration of plasticizers when the support is made of a material such as non-plasticized vinyl chloride in which plasticizers can readily migrate, whereas use of branched alcohols having more than 18 carbon atoms may result in a reduction in the compatibility with the acrylic polymer. Accordingly, it is preferable that branched alcohols having 14 to 18 carbon atoms are used.

Examples of the esters of monobasic or polybasic acids having 8 to 18 carbon atoms and branched alcohols having 14 to 18 carbon atoms include isostearyl laurate, isocetyl myristate, octyldodecyl myristate, isostearyl palmitate, isocetyl stearate, octyldodecyl oleate, diisostearyl adipate, diisocetyl sebacate, trioleyl trimellitate, and triisocetyl trimellitate. Further, examples of the unsaturated fatty acid or branched acids having 14 to 18 carbon atoms include myristoleic acid, oleic acid, rinolic acid, rinolenic acid, isopalmitic acid, isostearic acid. Examples of the tetrahydric or less alcohols include ethylene glycol, propylene glycol, glycerol, trimethylolpropane, pentaerythritol and sorbitan.

The pressure-sensitive adhesive used in the present invention preferably contains 30 to 100 parts by weight of the compatible component per 100 parts by weight of the acrylic polymer. It is more preferable that the compatible component is contained in amounts of 30 to 80 parts by weight per 100 parts by weight of the acrylic polymer.

In the present invention, it is preferable that the compatible component is blended with a non-crosslinked acrylic polymer and the resultant is subjected to crosslinking treatment such that 40 to 80% by weight of the acrylic polymer is insolubilized to form a pressure-sensitive adhesive layer. Thus, crosslinking treatment to the acrylic polymer increases cohesive force of the pressure-sensitive adhesive and allows it to exhibit moderate tack strength.

Examples of the crosslinking treatment include physical treatment methods such as γ ray irradiation and electron beam irradiation, and chemical treatment methods using organic peroxides, isocyanate compounds, organometal salts, metal alcoholates, metal chelate compounds, epoxy group containing compounds, primary amino group containing compounds. From the viewpoints of readiness of blending a pressure-sensitive adhesive and readiness of adjusting degree of crosslinking, it is preferable that chemical crosslinking treatment methods using isocyanate compounds, metal alcoholates and metal chelate compounds are applied. In this case, it is preferable that the amount of crosslinking agent blended is controlled so that 40 to 80% by weight of the acrylic polymer is insolubilized. If the insolubilization rate of the acrylic polymer is less than 40%, the cohesive force of the pressure-sensitive adhesive is insufficient, so that the pressure-sensitive adhesive may remain on the skin or the pressure-sensitive adhesive may run out from the side of the bandage, so that in the case where the support is made of a porous material such as nonwoven fabric, there may occur so-called strikethrough, the phenomenon that the pressure-sensitive adhesive penetrates the support layer to the backside thereof. On the other hand, if the insolubilization rate exceeds 80%, the pressure-sensitive adhesive layer may obtain only insufficient adhesion to the skin.

The compatible components that are in a liquid or paste state used in the present invention may include those that contain unsaturated double bonds. When such compatible components are used, it is preferable that an antioxidant is used in order to stabilize the composition.

The support layer that constitutes the pressure-sensitive adhesive sheets of the present invention contains the compatible component that is compatible with the acrylic polymer and is in a liquid or paste state at room temperature as stated above. The support layer in a state where it contains no compatible component has an elongation of 200% or more. That is, when tensile tests are performed at an elongation rate of 300 mm/minute, it has an elongation of 200% or more.

The support layer that has an elongation of less than 200% allows migration of less compatible component and causes no swelling deformation but has poor followability to the skin and the like. On the other hand, generally speaking, support layers that elongate well tend to absorb the compatible component and swell to deform. However, preliminarily blending the compatible component in a base resin that constitutes a support layer that elongates well can prevent the swelling and deformation of the support layer. In this case, the amount of the compatible component blended in the support layer may be determined appropriately depending on the amount of the compatible component absorbed by the support layer and the amount of the compatible component to be added to the pressure-sensitive adhesive. For example, the amount of the compatible component to be blended in the support layer must be 70% or less (but more than 0%), preferably 10% or more and 50% or less of the amount of the compatible component to be blended in the pressure-sensitive adhesive. If the amount of the compatible component blended in the support layer is too large, the strength of the support layer is decreased, so that the strength required for pressure-sensitive adhesive sheets cannot be obtained and their handleability is decreased, whereas if no compatible component is blended, the occurrence of swelling deformation cannot be prevented, so that the processability of pressure-sensitive adhesive sheets is decreased. In the present invention, the compatible component to be added to the support layer is not particularly limited, however, it is preferable that the compatible component that has the same composition as that blended in the pressure-sensitive adhesive is blended in order not to give adverse effects to the pressure-sensitive adhesive.

Example of the base resin that forms the support layer include olefin resins such as polyethylenes, polypropylenes, and ethylene/vinyl acetate copolymers (EVA), acrylic resins, vinyl chloride resins, polyether-urethane resins, polyester-polyurethane resins, and urethane-acrylic composite polymers. These resins may be blended as necessary. Further, crosslinking agents, fillers, pigments, antioxidants, ultraviolet absorbents and the like may be blended as necessary. The urethane-acrylic composite polymers, which are composites of urethane polymers and acrylic polymers, have excellent anchoring effects with the pressure-sensitive adhesive layer and use of them makes it easy to modify the physical properties of the support layer. Accordingly, it is particularly preferable that the urethane-acrylic composite polymers are used in the present invention. The term "composite" or "composite material" as used herein refers to so-called "polymer alloy", which is in a state where two or more kinds of polymers are mixed on the order of micrometer to form a uniform phase macroscopically. Generally speaking, blends of different kinds of polymers are macroscopically phase-separated and have properties that are average of the properties of respective polymers. In contrast, the composite material often exhibits new physical properties in addition to the average properties.

Hereinafter, a method for obtaining urethane-acrylic composite polymers will be described. That is, an aqueous dispersion of urethane-acrylic polymer that is nontacky at room temperature can be produced by a) preparing an aqueous dispersion of urethane-acrylic composite polymer resin, b) adding, to the dispersion, a nontackifying monomer that is composed mainly of an alkyl (meth)acrylate and that shows a glass transition temperature of 273K or more as a polymer, and polymerizing the resultant mixture.

In the step a), the aqueous dispersion of urethane-acrylic composite is prepared by either (i) or (ii) below. That is, (i) the aqueous dispersion is prepared by mixing a monomer composed mainly of an alkyl (meth)acrylate with a carboxyl group-containing urethane prepolymer synthesized using a polyol and a polyisocyanate, neutralizing the carboxyl group in the carboxyl group-containing urethane prepolymer to disperse the monomer in water, extending the main chain of the carboxyl group-containing urethane prepolymer by reaction of isocyanate group therein to perform polymerization of the monomer mixture. Alternatively, (ii) the aqueous dispersion is produced by mixing a polymer having at least one carboxyl group and at least one hydroxyl group in the molecule obtained by copolymerization of a monomer mixture composed mainly of an alkyl (meth)acrylate and a carboxyl group-containing monomer as an acrylic component with a polyol, reacting the resulting mixture with a polyisocyanate to synthesize an isocyanate prepolymer, neutralizing the carboxyl group of the isocyanate prepolymer to disperse the prepolymer in water, and extending the main chain thereof by reaction with at least one isocyanate group of the isocyanate prepolymer.

Here, the polyol that constitutes the urethane is preferably a polyol having two or more hydroxyl groups in the molecule. Examples of low molecular weight polyol include dihydric alcohols such as ethylene glycol, diethylene glycol, propylene glycol, butylene glycol, and hexamethylene glycol, trihydric or tetrahydric alcohols such as trimethylolpropane, glycerol, and pentaerythritol, and the like.

Further, examples of high molecular weight polyols include polyether polyols, polyester polyols, acrylic polyols, epoxy polyols and so on. The polyether polyols include polyethylene glycol, polypropylene glycol, and polytetramethylene glycol. The polyester polyols include polycondensation products between alcohols such as the above-mentioned dihydric alcohols, dipropylene glycol, 1,4-butanediol, 1,6-hexanediole and neopentyl glycol and dibasic acids such as adipic acid, azelaic acid, and sebacic acid. In addition, mention may be made of lactone ring opening polymerized polyol polycarbonate diol such as polycaprolactone. The acrylic polyols include copolymers of hydroxyl group-containing monomers such as hydroxyethyl (meth)acrylate and hydroxypropyl (meth)acrylate as well as copolymers of hydroxyl group-containing compounds and acrylic monomers and so on. The epoxy polyols include amine-modified epoxy resins and the like.

These polyols may be used singly or as combinations.

The polyisocyanates that constitute the urethane include aromatic, aliphatic and alicyclic diisocyanates, dimers, trimers, etc. of the diisocyanates. The aromatic, aliphatic and alicyclic diisocyanates include tolylene diisocyanate, diphenylmethane diisocyanate, hexamethylene diisocyanate, xylylene diisocyanate, hydrogenated xylylene diisocyanate, isophorone diisocyanate, hydrogenated diphenylmethane diisocyanate, 1,5-naphthylene diisocyanate, 1,3-phenylene diisocyanate, 1,4-phenylene diisocyanate, butane-1,4-diisocyanate, 2,2,4-trimethylhexamethylene diisocyanate, 2,4,4-trimethylhexamethylene diisocyanate, cyclohexane-1,4-diisocyanate, dicyclohexylmethane-4,4-diisocyanate, 1,13-bis (isocyanatomethyl)cyclohexane, methylcyclohexane diisocyanate, and m-tetramethylxylylene diisocyanate. Also, dimers, trimers of these and polyphenylmethane polyisocyanates may be used. The trimers include isocyanurate types, biuret types, allophanate types and the like, and these may be used as appropriate.

These polyisocyanates may be used singly or as combinations. It is particularly preferable that alicyclic polyisocyanates, which react with polyols rapidly and have low reactivity with water, are used. For example, alicyclic diisocyanates may be used.

The amounts of polyol and polyisocyanate used for forming the urethane polymer are not particularly limited. For example, the amount of polyol used in relation to the amount of polyisocyanate used is preferably such that NCO/OH (equivalent ratio) is 0.8 or more, more preferably 0.8 to 4.0, and particularly 0.8 to 3.0. If the NCO/OH is less than 0.8, the chain length of the urethane polymer cannot be extended sufficiently, so that the strength and elongation of films tend to be decreased. Further, if NCO/OH is 3.0 or less, the flexibility of films can be maintained sufficiently.

In the reaction between isocyanate and hydroxyl group of the polyol, a catalyst may be used. For example, those catalysts that are commonly used in urethane reactions, such as dibutyltin dilaurate, tin octoate, and 1,4-diazabicyclo [2,2,2] octane may be used.

The alkyl (meth)acrylate is preferably one that has 1 to 14 carbon atoms in the alkyl group. The carboxyl group-containing monomers include (meth)acrylic acid, maleic acid, itaconic acid and the like.

As the nontackifying monomer in the step b), those monomers composed mainly of alkyl (meth)acrylate had have a glass transition temperature of 273K or more, preferably 300K or more as a polymer are used advantageously. The acrylic component may include copolymerizable monomers other than these.

It is preferable that the blending ratio of the urethane-acrylic composite dispersion is adjusted such that the solids content of the urethane-acrylic composite dispersion is in amounts of 20 to 90% by weight and the nontackifying monomer is in amounts of 80 to 10% by weight and finally, the polyol component is in amounts of 10 to 50% by weight, the polyisocyanate component is in amounts of 2 to 20% by weight, and the acrylic component is in amounts of 40 to 90% by weight.

The medical pressure-sensitive adhesive sheets of the present invention can be obtained by forming a pressure-sensitive adhesive layer on one or both sides of a support layer with a pressure-sensitive adhesive.

That is, (a) a mixture of a base resin for forming a support layer and a compatible component and optionally additives and the like is applied on a release treated side of a release liner (release material) by, for example, extrusion molding to form the support layer. Separately, a coating solution for a pressure-sensitive adhesive layer containing an acrylic polymer, a compatible component and optionally additives and the like is coated on a release treated side of a release liner (release material) to form the pressure-sensitive adhesive layer. The obtained support layer and pressure-sensitive adhesive layer are laminated to produce a medical pressure-sensitive adhesive sheet having a pressure-sensitive adhesive layer on at least one side of the support layer.

Alternatively, (b) a medical pressure-sensitive adhesive sheet having a pressure-sensitive adhesive layer on one or both sides of a support can be produced as follows. A mixture of a base resin for forming a support layer and a compatible component and optionally additives and the like is applied on a release treated side of a release liner (release material) by, for example, extrusion molding to form the support layer. A coating solution for a pressure-sensitive adhesive layer containing an acrylic polymer, a compatible component and optionally additives and the like is coated on one or both sides of the support layer to form a pressure-sensitive adhesive layer. In this manner, a medical pressure-sensitive adhesive sheet having a pressure-sensitive adhesive layer on at least one side of the support layer can be produced.

In (a) and (b) above, the method for forming the support layer may be a method in which a compatible component and the like are added to a base resin in the form of, for example, pellets and the resultant is shaped into a form of a sheet by, for example, extrusion molding, a method in which a compatible component is directly added to an aqueous dispersion, for example, of urethane-acrylic composite polymer and the like and the resultant is shaped into a form of sheet, or a method in which after a base resin and the like is shaped into a form of a sheet, the sheet is immersed in a solution of a compatible component to impregnate the sheet with an appropriate amount of the solution.

Further, it is preferable that the pressure-sensitive adhesive layer, which is formed either by blending a non-crosslinked acrylic polymer with a compatible component, coating the resultant mixture directly on at least one side of the support layer and drying the mixture, or by preliminarily coating the mixture on a release liner, drying the mixture, and laminating the resultant to the support layer, is subjected to crosslinking treatment such that 40 to 80% by weight of the non-crosslinked acrylic polymer is insolubilized. The crosslinking method may be any method that is selected from physical treatments, chemical treatments and the like. The coating method is selected appropriately. Drying conditions under which no foaming or cracking in the resulting film occurs are selected as appropriate. In addition, it is preferable that the coating film is dried, for example, by applying heat from the side of the release liner (release material) because a membrane tends to be formed on the surface of the coating film if the coating film is dried from the surface.

Further, the surface of the pressure-sensitive adhesive layer may be protected by retaining the release liner until use.

The medical pressure-sensitive adhesive sheets of the present invention thus formed can prevent the deformation of the support layer, have excellent processability, and excellent pressure-sensitive adhesive properties such as moderate tack strength and holding power, and can suppress physical stimulation given to the adherend upon peeling off to low levels. Note that the pressure-sensitive adhesive sheets that have a pressure-sensitive adhesive layer on both sides the support layer serve as pressure-sensitive adhesive double coated sheets and the pressure-sensitive adhesive properties can be altered by adjusting the composition and thickness of the support layer. Further, varying the physical properties and thickness of the support layer results in broadening the range in which the properties are varied, which makes it possible to cover various applications. The pressure-sensitive adhesive sheets that have a pressure-sensitive layer only on one side of the support layer can be given performance suitable for respective applications by varying the pressure-sensitive adhesive properties or adjusting the physical properties of the support layer in the same manner as in the case of the pressure-sensitive adhesive double coated sheets.

The release material that can be used include those made of paper, laminated paper, various kinds of plastic films, metal foils and the like, treated with silicone on at least one side thereof. Release materials of any shape, such as sheet, tape, or belt may be used. The release material may be removed by peeling after a laminate of a pressure-sensitive adhesive layer, a support layer and the like is formed. However, it may be left as it is a release liner until use in order to protect the pressure-sensitive adhesive layer.

The thickness of each layer of the pressure-sensitive adhesive sheet is not particularly limited and is preferably set appropriately depending on the application and purpose. It is preferably that, for example, the support layer has a thickness in the range of preferably 10 to 150 μm and the pressure-sensitive adhesive layer has a thickness in the range of preferably 10 to 150 μm. Note that the support layer may be formed by adding a foaming agent to the aqueous polymer dispersion for forming a support layer, coating the dispersion and then foaming so as to have cushioning properties. In this case, the thickness of the support layer may be 50 to 2,000 μm.

The medical pressure-sensitive adhesive sheets of the present invention may be used in various forms such as sheets, tapes and the like having various sizes. Further, the medical pressure-sensitive adhesive sheets of the present invention may be stored with roll-shaped forms. These medical pressure-sensitive adhesive sheets can be used in the field of medical hygine, external application and the like, for example, can be advantageously applied to adhesive bandages, pressure-sensitive bandages, dressing materials and the like.

EXAMPLES

Hereinafter, the present invention will be described in more detail by referring to examples. However, the present invention should not be considered to be limited thereto and various applications are possible without departing the scope of technical idea of the present invention. Note that all parts in the following examples are by weight. The measuring method and evaluation method used in the examples are described below.

<Measuring Method and Evaluation Method>

(1) Tensile Test

Samples of 50 mm in length were prepared using a material for support layer without containing any compatible component so as to have a cross-section area of 1 mm$^2$. The samples were subjected to tensile tests on a tensile testing machine ("Autograph AGS-50D Model", manufactured by Shimadzu Corporation) at a chuck distance of 20 mm and an elongation speed of 300 mm/minute and the lengths at which the samples were broken were measured. Elongation of the samples was obtained according to the following equation.

Elongation (%)={Length of sample at break (mm)/20(mm)}×100.

(2) Processability

Pressure-sensitive adhesive sheets of which crosslinking reaction was completed by heating were punched using a Thompson blade. The appearance of the punched pressure-sensitive adhesive sheet was observed with naked eye and evaluation was made based on the following criteria.

Evaluation Criteria:

"○" The case where a pressure-sensitive adhesive sheet having the same size as that of the punch blade.

"×" The case where a partial shear occurred in the cut surface and a pressure-sensitive adhesive sheet having a different size from that of the punch blade.

(3) Deformation Rate

Immediately after the pressure-sensitive adhesive sheet was prepared, it was cut to a size of 50 mm×50 mm, and the size of one side was measured (here, referred to as "initial value"). The cut pressure-sensitive adhesive sheet was maintained at 60° C. for 3 days and then the size of the side was measured (here, referred to as "value after storage"). The deformation of the pressure-sensitive adhesive sheet was calculated according to the following equation.

Deformation rate (%)=[(Value after storage−Initial value)/Initial value]×100

Example 1

<Formation of Pressure-Sensitive Adhesive Layer>

In an inert gas atmosphere, a monomer mixture consisting of 95 parts of 2-ethylhexyl acrylate and 5 parts of acrylic acid was polymerized to prepare an acrylate polymer. 100 parts of the obtained acrylate polymer, 40 parts of isopropylmyristate, and 0.06 part of trifunctional isocyanate ("Coronate HL", manufactured by Nippon Polyurethane Co., Ltd.) were mixed in ethyl acetate to prepare a pressure-sensitive adhesive solution. The obtained pressure-sensitive adhesive solution was coated on a release liner made of polyester to a dry thickness of 60 μm and dried at 110° C. for 5 minutes to prepare a pressure-sensitive adhesive layer.

<Formation of Support Layer>

To 100 parts of polypropylene glycol having a number average molecular weight of 3,000 were added a monomer mixture consisting of 45 parts of butyl acrylate, 45 parts of ethyl acrylate, and 10 parts of acrylic acid, 2 parts of 2-mercaptoethanol as a chain transfer agent having a hydroxyl group, 0.1 part of 2,2-azobisisobutyronitrile as a polymerization initiator and the resultant was subjected to polymerization reaction in a nitrogen stream at 60° C. for 4 hours to obtain a viscous liquid composed of a mixture of polypropylene glycol and an acrylic polymer having a number average molecular weight of 7,500.

To the viscous liquid was added 23.5 parts of isophorone diisocyanate (2.3 times equivalent based on total hydroxyl groups), and reaction was performed at 65° C. for 3 hours to synthesize an isocyanate prepolymer. After 14 parts (identical equivalent with respect to carboxyl group) of triethylamine was added to the isocyanate prepolymer to neutralize the carboxyl group, 600 parts of water was added with stirring to disperse the isocyanate prepolymer in water. Then, a solution obtained by diluting 1.8 parts (identical equivalent with respect to the remaining isocyanate group) of ethylenediamine with 16.2 parts of water was added and reaction was performed at 65° C. for 3 hours to extend the main chain.

A nontackifying monomer mixture consisting of 113.7 parts of isobornyl acrylate (having a glass transition temperature of 367K as a polymer) was added to the urethane-acrylic composite aqueous dispersion thus obtained with stirring to allow the nontackifying monomer mixture to be absorbed by the urethane-acrylic core polymer particles in the urethane-acrylic composite aqueous despersion. Then, 0.11 part of 2,2-azobis [2-(2-imidazolin-2-yl)]propane was added to initiate polymerization reaction and the resultant was maintained at 60° C. for 4 hours. Thereafter, the temperature was elevated to 70° C. and maintained for 1 hour, followed by cooling. This polymerization treatment gave a urethane-acrylic composite aqueous dispersion having stably dispersed in water a urethane-acrylic polymer consisting of 29% by weight of a polyol component, 7% by weight of a polyisocyanate component, and 63% by weight of an acrylic component (and the balance components containing a neutralizing agent, urethane main chain extending agent and so on) and having no pressure-sensitive adhesive property at room temperature.

To the urethane-acrylic composite aqueous dispersion was added 10 parts of isopropyl myristate (corresponding to 25% of the amount of isopropyl myristate blended with the pressure-sensitive adhesive) and mixed homogeneously. Then the mixture was coated on release treated polyester film and dried at 110° C. for 5 minutes to prepare a uniform film (support layer) having a thickness of 50 μm. Note that the support layer had an elongation of 400% without addition of isopropyl myristate.

<Preparation of Pressure-Sensitive Adhesive Sheet>

The obtained pressure-sensitive adhesive layers were transferred to the obtained support layers to prepare medical pressure-sensitive adhesive sheets. The obtained pressure-sensitive adhesive sheets were evaluated for processability and deformation rate. The results obtained are shown in Table 1.

Example 2

A pressure-sensitive adhesive layer was prepared in the same manner as in Example 1 except that the blending amount of isopropyl myristate was changed to 60 parts.

10 parts of isopropyl myristate (corresponding to 16.7% of the amount of isopropyl myristate blended with the pressure-sensitive adhesive) were blended with 100 parts of urethane resin pellets, and the resultant was melt extruded at 230° C. to prepare a uniform film (support layer) having a thickness of 30 μm. Note that the support layer had an elongation of 550% without containing isopropyl myristate.

Then, a medical pressure-sensitive adhesive sheet was prepared by transferring the pressure-sensitive adhesive layer to the support layer in the same manner as in Example 1. The obtained pressure-sensitive adhesive sheet was evaluated in the same manner as in Example 1. The results obtained are shown in Table 1.

Example 3

A pressure-sensitive adhesive layer was prepared in the same manner as in Example 1 except that 50 parts of sorbitan trioleate was blended in place of isopropyl myristate as the compatible component.

A 50 μm thick EVA film was immersed in sorbitan trioleate at 50° C. for 3 days to form a support layer containing 5 parts of sorbitan trioleate (corresponding to 10% of the sorbitan trioleate blended in the pressure-sensitive adhesive layer). Note that the EVA film had an elongation of 500% before immersion in sorbitan trioleate.

Then, a medical pressure-sensitive adhesive sheet was prepared by transferring the pressure-sensitive adhesive layer to the support layer in the same manner as in Example 1. The obtained pressure-sensitive adhesive sheet was evaluated in the same manner as in Example 1. The results obtained are shown in Table 1.

Example 4

A pressure-sensitive adhesive layer was prepared in the same manner as in Example 1 except that 60 parts of sorbitan trioleate was blended in place of isopropyl myristate as the compatible component.

A film (support layer) was prepared in the same manner as in Example 1 except that 33 parts of sorbitan trioleate was blended in place of isopropyl myristate as the compatible component. Note that the support layer had an elongation of 400% without containing sorbitan trioleate.

Then, a medical pressure-sensitive adhesive sheet was prepared by transferring the pressure-sensitive adhesive layer to the support layer in the same manner as in Example 1. The obtained pressure-sensitive adhesive sheet was evaluated in the same manner as in Example 1. The results obtained are shown in Table 1.

Comparative Example 1

A medical pressure-sensitive adhesive sheet was prepared in the same manner as in Example 1 except that the amount of the isopropyl myristate blended in the urethane-acrylic composite aqueous dispersion was changed to 40 parts (corresponding to 100% of the amount of isopropyl myristate blended in the pressure-sensitive adhesive layer).

The obtained pressure-sensitive adhesive sheet was evaluated in the same manner as in Example 1. The results obtained are shown in Table 1.

Comparative Example 2

It was tried to prepare a pressure-sensitive adhesive sheet in the same manner as in Example 2 except that the amount of the isopropyl myristate blended in the urethane-acrylic composite aqueous dispersion was changed to 50 parts (corresponding to 83.3% of the amount of isopropyl myristate blended in the pressure-sensitive adhesive layer). However, defects (holes) occurred in the support layer and thus no pressure-sensitive adhesive sheet was obtained.

Comparative Example 3

A medical pressure-sensitive adhesive sheet was prepared in the same manner as in Example 3 except that the support layer was prepared without immersing the EVA film in sorbitan trioleate.

The obtained pressure-sensitive adhesive sheet was evaluated in the same manner as in Example 1. The results obtained are shown in Table 1.

TABLE 1

| | Kind of Compatible Component | Compatible component Support layer/ Pressure-sensitive layer (%) | Elongation (%) | Processability | Deformation rate (%) |
|---|---|---|---|---|---|
| Example 1 | Isopropyl myristate | 25 | 400 | ○ | 0 |
| Example 2 | Isopropyl myristate | 16.7 | 550 | ○ | 0 |
| Example 3 | Sorbitan trioleate | 10 | 500 | ○ | 0 |
| Example 4 | Sorbitan trioleate | 55 | 400 | ○ | 0 |
| Comparative Example 1 | Isopropyl myristate | 100 | 400 | X | 0.8 |
| Comparative Example 2 | Isopropyl myristate | 83.3 | 550 | No pressure-sensitive adhesive sheet | |
| Comparative Example 3 | Sorbitan trioleate | 0 | 500 | X | 1.0 |

Table 1 indicates that the medical pressure-sensitive adhesive sheets of Examples 1 to 4 showed no deformation due to migration of the compatible component and that they had acceptable processability. Further, the pressure-sensitive adhesive sheets of the present invention had moderate tack strength and gave less physical stimulation to an adherend when it was peeled from the adherend and had excellent followability to the skin and the like.

On the other hand, the pressure-sensitive adhesive sheets of Comparative Examples 1 and 3 revealed to have high deformation rate and poor processability. Further, in Comparative Example 2, defects occurred during formation of the support layer, so that no pressure-sensitive adhesive sheet could be obtained.

According to the present invention, there can be provided medical pressure-sensitive adhesive sheets that have acceptable tack strength and acceptable processability so that physical stimulation given to an adherend when they are peeled from the adherend can be maintained to low levels and of which supports do not undergo swelling deformation. Also there can be provided a method for producing such medical pressure-sensitive adhesive sheets.

The invention claimed is:

1. A medical pressure-sensitive adhesive sheet comprising a support layer having a pressure-sensitive adhesive layer on at least one side thereof, wherein the pressure-sensitive adhesive layer is formed with an adhesive comprising 100 parts by weight of an acrylic polymer and 30 to 100 parts by weight of a compatible component that is compatible with the acrylic polymer and that is in a liquid or paste state at room temperature and wherein the support layer contains a compatible component that is compatible with the acrylic polymer and that is in a liquid or paste state at room temperature, the amount of the compatible component contained in the support layer is more than 0% and 70% or less of the amount of the compatible component contained in the pressure-sensitive adhesive layer, and the support layer has an elongation of 200% or more in a state where the support layer contains no compatible component, and wherein the support layer is formed with a resin composition that contains a urethane-acrylic composite polymer.

2. The medical pressure-sensitive adhesive sheet according to claim 1, wherein the urethane-acrylic composite polymer is obtained by preparing a urethane-acrylic polymer composite aqueous dispersion, adding thereto a nontackifying monomer comprising an alkyl (meth)acrylate and having a glass transition temperature of 273°K or more as a polymer, and subjecting the resultant mixture to a polymerization treatment.

3. The medical pressure-sensitive adhesive sheet according to claim 1, wherein the compatible component is an ester of a monobasic acid having 8 to 18 carbon atoms or a polybasic acid having 8 to 18 carbon atoms with a branched alcohol having 14 to 18 carbon atoms, and an ester of an unsaturated fatty acid having 14 to 18 carbon atoms or a branched acid having 14 to 18 carbon atoms with a tetrahydric or lower alcohol.

4. The medical pressure-sensitive adhesive sheet according to claim 1, wherein the compatible component is an ester of a monobasic acid having 8 to 18 carbon atoms or a polybasic acid having 8 to 18 carbon atoms with a branched alcohol having 14 to 18 carbon atoms, or an ester of an unsaturated fatty acid having 14 to 18 carbon atoms or a branched acid having 14 to 18 carbon atoms with a tetrahydric or lower alcohol.

5. The medical pressure-sensitive adhesive sheet according to claim 1, wherein 40 to 80% by weight of the acrylic polymer contained in the pressure-sensitive adhesive layer is insolubilized.

6. A medical pressure-sensitive adhesive sheet comprising a support layer having a pressure-sensitive adhesive layer on at least one side thereof, wherein the pressure-sensitive adhesive layer is formed with an adhesive comprising 100 parts by weight of an acrylic polymer and 30 to 100 parts by weight of a compatible component that is compatible with the acrylic polymer and that is in a liquid or paste state at room temperature and wherein the support layer contains a compatible component that is compatible with the acrylic polymer and that is in a liquid or caste state at room temperature, the amount of the compatible component contained in the support layer is more than 0% and 70% or less of the amount of the compatible component contained in the pressure-sensitive adhesive layer, and the support layer has an elongation of 200% or more in a state where the support layer contains no compatible component, wherein the support layer is formed with a resin composition that contains a urethane-acrylic composite polymer, and wherein the compatible component contained in the support layer and the compatible component contained in the pressure-sensitive adhesive layer have the same composition.

7. The medical pressure-sensitive adhesive sheet according to claim 6, wherein the urethane-acrylic composite polymer is obtained by preparing a urethane-acrylic polymer composite aqueous dispersion, adding thereto a nontackifying monomer comprising an alkyl (meth)acrylate and having a glass transition temperature of 273°K or more as a polymer, and subjecting the resultant mixture to a polymerization treatment.

8. The medical pressure-sensitive adhesive sheet according to claim 6, wherein 40 to 80% by weight of the acrylic polymer contained in the pressure-sensitive adhesive layer is insolubilized.

9. The medical pressure-sensitive adhesive sheet according to claim 6, wherein the compatible component is an ester of a monobasic acid having 8 to 18 carbon atoms or a polybasic acid having 8 to 18 carbon atoms with a branched alcohol having 14 to 18 carbon atoms, and an ester of an unsaturated fatty acid having 14 to 18 carbon atoms or a branched acid having 14 to 18 carbon atoms with a tetrahydric or lower alcohol.

10. The medical pressure-sensitive adhesive sheet according to claim 6, wherein the compatible component is an ester of a monobasic acid having 8 to 18 carbon atoms or a polybasic acid having 8 to 18 carbon atoms with a branched alcohol having 14 to 18 carbon atoms, or an ester of an unsaturated fatty acid having 14 to 18 carbon atoms or a branched acid having 14 to 18 carbon atoms with a tetrahydric or lower alcohol.

* * * * *